(12) United States Patent
Johann et al.

(10) Patent No.: US 7,468,463 B2
(45) Date of Patent: Dec. 23, 2008

(54) METHOD FOR PRODUCING OPTICALLY ACTIVE CARBONYL COMPOUNDS

(75) Inventors: Thorsten Johann, Limburgerhof (DE); Oliver Löber, Freimersheim (DE); Eike Johannes Bergner, Schriesheim (DE); Klaus Ebel, Lampertheim (DE); Klaus Harth, Tai Tam (CN); Christian Walsdorff, Ludwigshafen (DE)

(73) Assignee: BASF AG (DE)

( * ) Notice: Subject to any disclaimer, the term of this patent is extended or adjusted under 35 U.S.C. 154(b) by 0 days.

(21) Appl. No.: 10/591,925

(22) PCT Filed: Mar. 4, 2005

(86) PCT No.: PCT/EP2005/002288

§ 371 (c)(1),
(2), (4) Date: Sep. 5, 2006

(87) PCT Pub. No.: WO2005/085160

PCT Pub. Date: Sep. 15, 2005

(65) Prior Publication Data

US 2007/0191644 A1    Aug. 16, 2007

(30) Foreign Application Priority Data

Mar. 8, 2004   (DE) .................. 10 2004 011 543

(51) Int. Cl.
*C07C 45/65* (2006.01)
(52) U.S. Cl. .................. 568/338; 568/361; 568/366
(58) Field of Classification Search .............. 568/338, 568/361, 366
See application file for complete search history.

(56) References Cited

U.S. PATENT DOCUMENTS

| 2,990,422 | A  | * | 6/1961  | Cole et al. ............... 558/293 |
| 6,162,758 | A  |   | 12/2000 | Bröcker et al. |
| 6,433,229 | B1 |   | 8/2002  | Fischer et al. |
| 6,518,220 | B2 |   | 2/2003  | Walsdorff et al. |
| 6,716,789 | B1 |   | 4/2004  | Heineke et al. |

FOREIGN PATENT DOCUMENTS

| CN | 1059710     | 3/1992  |
| CN | 1059711     | 3/1992  |
| DE | 42 36 111   | 4/1994  |
| DE | 197 57 297  | 6/1999  |
| DE | 199 11 169  | 9/2000  |
| EP | 1 225 163   | 7/2002  |
| JP | 51-149217   | 12/1976 |
| WO | WO-97/33853 | 9/1997  |

OTHER PUBLICATIONS

Doeuvre, Bulletin de la Societe Chimique de France, Bd, 45, 1929, pp. 1098-1107 (translation of relevant sections).
Fan Cun-liang et al., *Development of Process for Synthesizing L-Menthol*, Flavour Fragrance Cosmetics, No. 4, Aug. 2002.

* cited by examiner

*Primary Examiner*—Sikarl A Witherspoon
(74) *Attorney, Agent, or Firm*—Connolly Bove Lodge & Hutz LLP

(57) ABSTRACT

The present invention relates to a process for preparing optically active aldehydes or ketones which have from 3 to 25 carbon atoms and at least one racemizable stereocenter by catalytic dehydrogenation of the corresponding optically active primary or secondary alcohols in the gas phase in the presence of a catalyst.

16 Claims, No Drawings

METHOD FOR PRODUCING OPTICALLY ACTIVE CARBONYL COMPOUNDS

RELATED APPLICATIONS

This application is a national stage application (under 35 U.S.C. 371) of PCT/EP2005/002288 filed March 4, 2005, which claims benefit to German application 102004 011 543.5 filed March 8, 2004.

The present invention relates to a process for preparing optically active aldehydes or ketones which have from 3 to 25 carbon atoms and at least one racemizable stereocenter.

Chiral aldehydes or ketones are important intermediates for the preparation of more valuable compounds. They themselves are of key importance as materials of value or active compounds in particular applications, for example the fragrances and flavors industry.

Owing to the difficulty of obtaining them, chiral aldehydes or ketones are often prepared or used in racemic form or are obtained in optically active form from natural sources. The preparation or reaction of optically active aldehydes or ketones on an industrial scale is often subject to severe limitations since these compounds are chemically, in particular stereochemically, labile and are therefore not compatible with many both industrially and economically attractive process and reaction conditions.

DE-A 199 11 169 describes a process for preparing cyclic α,β-unsaturated ketones by dehydrogenation of cyclic ketones at elevated temperature in the gas phase in the presence of a catalyst.

WO 97/33853 relates to a process for the dehydrogenation of secondary cyclic alcohols at elevated temperature in the gas phase in the presence of a catalyst comprising zinc oxide and calcium carbonate.

CN-A 1059710 and CN-A 1059711 describe a process for preparing camphor by dehydrogenation of isoborneol in the presence of catalysts based on CaO/ZnO. The reaction is carried out under a reduced pressure of from 0 to 60 Torr.

It was an object of the present invention to provide a process which makes it possible to convert optically active alcohols having racemizable stereocenters into the corresponding optically active aldehydes or ketones by dehydrogenation and with substantial retention of the absolute configuration of the racemizable stereocenters.

This object has surprisingly been achieved according to the invention by provision of a process for preparing optically active aldehydes or ketones which have from 3 to 25 carbon atoms and at least one racemizable stereocenter by catalytic dehydrogenation of the corresponding optically active primary or secondary alcohols in the gas phase in the presence of a catalyst.

For the purposes of the present invention, optically active compounds are compounds which are able, either as such or in dissolved form, to rotate the plane of polarization of linearly polarized light passing through them. Compounds having a sterogenic center are nonracemic mixtures of the two enantiomers, i.e. mixtures in which the two enantiomers are present in unequal amounts. A suitable measure for describing this circumstance is the enantiomeric excess (ee) whose determination by appropriate methods, e.g. by gas chromatography, is known per se to those skilled in the art.

The term racemizable stereocenter refers, in particular, to an asymmetrically substituted carbon atom which under the action of particular reagents such as acids or bases or else free radicals is able to assume, at least in intermediate form, a trigonal-planar configuration with loss of the original stereochemical information. Particular mention may be made here of asymmetric carbon atoms which bear three non-hydrogen substitutents together with one hydrogen atom which can be abstracted, for example by means of suitable bases. Further examples which may be mentioned are the asymmetrically substituted tertiary carbinol centers. Asymmetric bridgehead atoms of bridged bicyclic or polycyclic compounds, for example, are not racemizable for the purposes of the present invention.

The process of the invention is suitable for the dehydrogenation of optically active primary and secondary alcohols which have from 3 to 25 carbon atoms and at least one racemizable stereocenter. In the case of the reaction of secondary alcohols, this does not refer to the carbon atom bearing the alcohol function to be dehydrogenated, which may likewise be asymmetrically substituted. If chiral alcohols are used in racemic form, the corresponding racemic aldehydes and ketones are obtained successfully. Preference is given to using the chiral primary or secondary alcohols in optically active form and obtaining the corresponding optically active aldehydes or ketones with substantial retention of the configuration of the racemizable stereocenter, i.e. with substantial suppression of the racemization of this stereocenter.

The process is of particular importance for the reaction of primary or secondary alcohols which are in optically active form and have a racemizable stereocenter in the α or β position relative to the alcohol function to be dehydrogenated. From these, aldehydes or ketones which are in optically active form and have a stereocenter in the α or β position relative to the resulting carbonyl function can be obtained by means of the process of the invention. The further substitution pattern or the number of substitutents of the chosen substrates is not critical and is in general limited only by the stability of the substitutents or the compound to be reacted under the chosen reaction conditions.

The process of the invention is particularly useful for the dehydrogenation of optically active cycloaliphatic or open-chain primary and secondary alcohols which have at least one racemizable stereocenter and may be branched or unbranched and can have from 3 to 25, preferably from 5 to 12, carbon atoms to the corresponding optically active aldehydes or ketones. Branched or unbranched, open-chain or monocyclic aldehydes or ketones having at least one racemizable stereocenter are then obtained according to the invention. The alcohols to be dehydrogenated can also have one or more, in general from 1 to 3, olefinic double bonds which are stable under the reaction conditions.

The compounds mentioned can be used for the purposes of the invention as single compounds or in the form of mixtures of these, in particular, in the case of the reaction of compounds having more than one stereocenter, in the form of mixtures of diastereomers.

Preferred starting compounds for carrying out the process of the invention are optically active terpene alcohols, in particular optically active monoterpene or sesquiterpene alcohols, i.e. alcohols having 5, 10 or 15 carbon atoms and their derivatives. Examples which may be mentioned are the following compounds: 2-methylbutan-1-ol, 3,7-dimethyloct-6-en-1-ol (citronellol), 3,7-dimethyloctan-1-ol, 8-p-menthen-3-ol (isopulegol), p-menthan-3-ol (menthol), 2-methylcyclohexanol, 3-methylcyclohexanol, 2-methylcyclopentanol, 3-methylcyclopentanol, 2,6-dimethylcyclohexanol and 2,3-dimethylcyclohexanol.

From the compounds mentioned, the corresponding aldehydes or ketones are obtained according to the invention by dehydrogenation; examples of such aldehydes and ketones are: 2-methylbutan-1-al, 3,7-dimethyloct-6-en-1-al (citronellal), 3,7-dimethyloctan-1-al, 8-p-menthen-3-one (isopulegone), p-menthan-3-one (menthone), 2-methylcyclohexanone, 3-methylcyclohexanone, 2-methylcyclopentanone, 3-methylcyclopentanone, 2,6-dimethylcyclohexanone and 2,3-dimethylcyclohexanone.

The process is particularly useful for preparing optically active citronellal of the formula (I)

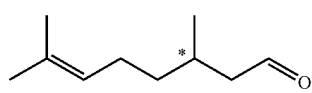

(I)

from optically active citronellol of the formula (II).

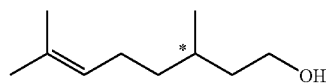

(II)

Both enantiomers of citronellol are naturally equally suitable as starting materials in the process of the invention. A preferred starting material is R-(+)-citronellol (D-citronellol).

Preference is given to using alcohols having an enantiomeric excess of at least 85% ee, particularly preferably at least 90% ee and very particularly preferably at least 95% ee, for the purposes of the present invention. The enantiomeric excess of the product aldehydes or ketones obtained according to the invention can be influenced by the choice of the enantiomeric excess in the starting material. It is particularly advantageous to select the reaction conditions, for example the reaction temperature, so that the enantiomeric excess of the product aldehyde or ketone obtained is at least about 90%, preferably at least about 95%, of the enantiomeric excess of the alcohol used.

A wide variety of catalysts, in particular catalysts comprising at least one element selected from the group consisting of the elements zinc, calcium and copper, in each case as such or in the form of suitable compounds, are suitable for carrying out the process of the invention.

Apart from the elements mentioned, the catalysts which can be used according to the invention may further comprise one or more elements of groups 1, 2, 3, 4, 13 and/or 14, e.g. Na, K, Mg, Ti, Zr, Al, C, Si and/or Ge.

Catalysts comprising zinc and calcium, preferably in oxidic form and/or in the form of their carbonates, are particularly useful for carrying out the dehydrogenation process of the invention. Particular preference is given to catalysts comprising zinc oxide and calcium carbonate.

Preferred catalysts for carrying out the process of the invention are catalysts whose active component comprises from 30 to 60% by weight, preferably from 40 to 50% by weight, of zinc oxide and from 40 to 70% by weight, preferably from 50 to 60% by weight, of calcium carbonates. Among these, further preference is given to those whose calcium carbonate component is present in the calcite modification. The proportions mentioned are to be determined from the ignited catalyst composition in which zinc and calcium are each present in the form of their oxides.

Further catalysts which can be used according to the invention are copper-comprising catalysts, in particular catalysts in which the copper is present in an oxidation state of >0 in a form deposited on an oxidic support, as are described in DE-A 197 57 297. As further support material, it is possible to use, for example, calcium carbonate and further suitable support materials.

In a preferred embodiment, the catalysts which can be used according to the invention have a specific surface area determined by the BET method of from 5 to 50 m$^2$/g, preferably from 10 to 30 m$^2$/g.

Such a catalyst can, for example, be obtained by precipitation of sparingly soluble zinc and calcium compounds from water-soluble zinc and calcium compounds by means of a base and subsequent work-up in a manner known per se, where (a) a water-soluble basic carbonate is used as base,
(b) if desired, the sparingly soluble zinc and calcium compounds are filtered off after precipitation,
(c) the zinc and calcium compounds, which have been filtered off if desired, are washed,
(d) the washed zinc and calcium compounds from (c) are dried to give a powder, and
(e) the powder from (d) is subsequently calcined at temperatures of not more than 600° C., and
(f) if desired, the calcined powder is pressed to form shaped bodies.

As water-soluble zinc and calcium salts, it is possible to use acetates, sulfates, nitrates, chlorides, preferably nitrates, e.g. zinc nitrate, zinc acetate, zinc sulfate, calcium acetate, calcium nitrate, preferably zinc nitrate and calcium nitrate. The aqueous solutions of the appropriate salts usually have concentrations in the range from 3 to 25% by weight, preferably from 10 to 25% by weight, in particular 20% by weight.

The molar ratio of zinc to calcium is preferably chosen so that the active component of the catalyst comprises from 30 to 60% by weight of zinc oxide and from 40 to 70% by weight of calcium carbonate, which is preferably present in the calcite modification, after calcination.

Bases used are preferably water-soluble basic carbonates such as alkali metal carbonates such as sodium carbonate, potassium carbonate, alkali metal hydrogencarbonates such as sodium hydrogencarbonate, potassium hydrogencarbonate, ammonium carbonate or ammonium hydrogencarbonate and also mixtures thereof, preferably sodium carbonate, particularly preferably in the form of its aqueous solutions having concentrations of generally from 0.5 to 30 gram of base/100 gram of solution, preferably from 10 to 25 gram of base/100 gram of solution.

The precipitation is generally carried out at temperatures in the range from 10 to 90° C., preferably from 40 to 80° C. After precipitation, the precipitate can be filtered off if desired. The precipitate which has been filtered off if desired is generally washed with water, preferably until nitrate can no longer be detected by means of the nitrate ring test, and is subsequently dried, preferably at a temperature in the range from 90 to 150° C., to give a dried powder. Drying can be carried out in a static or moving layer, preferably by spray drying.

The dried powder can then be calcined at temperatures of not more than 600° C., preferably in the range from 300 to 600° C., in particular from 400 to 475° C., preferably in air. On the basis of observations to date, prolonged heating at above 600° C. leads to formation of the aragonite modification of $CaCO_3$. Brief heating at above 600° C. does not cause a problem in the preparation of the preferred catalysts, as long as no aragonite (detected by means of X-ray diffractometry) is formed.

After calcination, the calcined powder can, if desired, be pressed to form shaped bodies such as pellets, rings, cylinders, etc., preferably pellets.

In a preferred embodiment, the calcined powder is pressed together with graphite, preferably with from 0.1 to 5% by weight, particularly preferably with from 1 to 2.5% by weight, in particular 2% by weight, based on the total mass, of graphite.

In a further, preferred embodiment, the uncalcined powder from step (c) (see above) is pressed to form shaped bodies, preferably pellets, annular pellets, pellets having domed ends as described in U.S. Pat. No. 6,518,220, or trilobes and the shaped bodies obtained in this way are calcined as described under step (d). As an alternative, extrusion to form extrudates or star extrudates, preferably extrudates, can also be carried out.

The resulting calcined powders and shaped bodies can be used as catalysts, with these catalysts being able to comprise zinc oxide and calcium carbonate (in the calcite modification) as active components and, if desired, graphite as passive component.

In a further, preferred embodiment, use is made of a catalyst of the type described which has a pore volume in the range from 0.10 to 0.50 cm$^3$/g, in particular from 0.20 to 0.35 cm$^3$/g, at a pore diameter in the range from 5 nm to 300 mm, with particular preference being given to at least 85%, preferably more than 90%, of this pore volume being associated with a pore diameter in the range from 0.01 to 0.5 mm.

Particularly preferred catalysts of the abovementioned type are catalysts which have an end face compressive strength in the range from 500 to 4000 N/cm$^2$, in particular from 1000 to 2500 N/cm$^2$, and a lateral compressive strength of from 30 to 300 N, preferably from 50 to 200 N.

The specific surface determined by the BET method is generally from 5 to 50 m$^2$/g, preferably from 10 to 30 m$^2$/g. The pore volume in the pore diameter range from 0.1 nm to 300 nm is usually in the range from 0.1 to 0.5 cm$^3$/g, preferably from 0.2 to 0.35 cm$^3$/g, with the proviso that at least 85%, preferably more than 90%, of this pore volume is in the pore diameter range from 0.01 to 0.5 mm.

The end face compressive strength of the pellets is preferably from 500 to 4000 N/cm$^2$, in particular from 1000 to 2500 N/cm$^2$ and the lateral compressive strength of the pellets is preferably in the range from 30 to 300 N, more preferably from 50 to 200 N.

It is particularly advantageous to wash the precipitate of sparingly soluble zinc and calcium compounds, preferably zinc hydroxide carbonate and calcium carbonate, on filter presses, slurry the resulting filter cake with water and dry the slurry by spraying in a spray dryer. The spray-dried powder obtained in this way can then be processed further as described above.

According to the invention the gaseous primary or secondary alcohol is brought into contact in a customary fashion with the catalyst used, for example in a fixed-bed reactor, tube reactor, shell-and-tube reactor or in a fluidized-bed reactor, preferably in a tube reactor in which the catalyst is present as a fixed bed. Particular preference is given to shell-and-tube reactors. The output is usually worked up by distillation.

In general, the optically active alcohol to be used according to the invention is vaporized in a manner known per se, for example in a suitable vaporizer.

The process of the invention is usually carried out at elevated temperature. The temperature of the gas phase in the reaction zone is usually in the range from 250 to 600° C., preferably from 300 to 450° C. In a preferred embodiment, the temperature range chosen is such that a conversion of alcohol in the range from 20 to 60%, preferably from 35 to 50%, is obtained. In the case of citronellol as starting compound, the temperature selected is preferably in the range from 350 to 450° C.

The pressure of the gas phase in the reaction zone is generally in the range from 0.3 to 10 bar.

The space velocity over the catalyst is generally in the range from 0.5 to 3.0 liters of alcohol per liter of catalyst and per hour, preferably from 0.6 to 2.0 liters of alcohol per liter of catalyst and per hour. Suitable forms of reactor for carrying out the process of the invention are fixed-bed tube reactors or shell-and-tube reactors. In these, the chosen catalyst is present as a fixed bed in a reaction tube or in a bundle of reaction tubes. The reaction tubes are usually heated indirectly by a gas, e.g. a hydrocarbon such as methane, being burnt in the space surrounding the reaction tubes or by a heat transfer medium (salt bath, circulating gas, etc.) being used. The reaction tubes can also be heated electrically using heating sleeves. The usual internal diameter of the reaction tube(s) is from about 2.5 to 15 cm. A typical shell-and-tube dehydrogenation reactor has from about 10 to 32000 reaction tubes, preferably from about 10 to 200 reaction tubes. The temperature in the interior of the tubes is usually in the range from 250 to 600° C., preferably in the range from 300 to 600° C. The working pressure is usually in the range from 0.5 to 8 bar, frequently from 1 to 2 bar.

The process of the invention can also be carried out in the presence of a heterogeneous catalyst in a fluidized bed, as described in Chem. Eng. Sci. 1992 b, 47 (9-11) 2313. In this case, it is advantageous to operate two fluidized beds in parallel, with one of these generally undergoing regeneration at a given time. The working pressure is typically from 1 to 2 bar, and the dehydrogenation temperature is generally from 250 to 600° C.

The catalytic dehydrogenation according to the invention can be carried out with or without an oxygen-containing gas as cofeed and optionally with addition of water vapor, nitrogen, methane and/or argon. The reactor selected can have one or more successive catalyst beds. The number of catalyst beds can be from 1 to 20, advantageously from 1 to 6, preferably from 1 to 4, and in particular from 1 to 3. The reaction gas preferably flows radially or axially through the catalyst beds. In general, such a tray reactor is operated using a fixed bed of catalyst. In the simplest case, the fixed beds of catalyst are arranged axially or in the annular gaps between concentric cylindrical meshes in a shaft furnace reactor. A shaft furnace reactor corresponds to one tray.

In a particularly preferred embodiment of the process of the invention, an optically active terpene alcohol, in particular citronellol, preferably R-(+)-citronellol, having an enantiomeric excess of at least 90% ee, preferably 95% ee, is reacted over a catalyst whose active component comprises from 54 to 57% by weight of zinc oxide and from 43 to 46% by weight of calcium carbonate (in each case determined in the form of the oxides in the ignited catalyst composition) in a suitable reactor, for example a tube reactor. The reactor can be heated by any suitable method, preferably by means of a salt melt, to temperatures in the range from about 350 to about 450° C. The reaction takes place in the gas phase. Good results are obtained particularly when the reaction is carried out in the absence of oxygen. For this purpose, a mixture comprising the starting material to be dehydrogenated is, for example, passed in a stream of inert gas, e.g. a stream of nitrogen, over the catalyst selected. Another option is autothermal operation by means of partial $H_2$ combustion after prior introduction of an $H_2$-containing mixture.

The isolation of the reaction products can be carried out by all suitable methods which are known per se to those skilled in the art. In this way, optically active citronellal is obtained in a selectivity of normally from about 60 to about 95% at a conversion of preferably from about 30 to about 60% of theory.

The optically active aldehydes or ketones which can be prepared according to the invention can be utilized in a variety of ways. They represent sometimes important starting materials or intermediates for the synthesis of more valuable products. Thus, for example, optically active citronellal, preferably R-(+)-citronellal, is an important intermediate for the synthesis of optically active menthol, preferably L-menthol. Thus, optically active citronellal can be cyclized in the presence of suitable catalysts, usually acid or Lewis-acid catalysts, to form optically active isopulegol. Optically active menthol can be obtained therefrom by hydrogenation. The use of optically active citronellal prepared according to the invention for preparing optically active menthol is accordingly a further aspect of the present invention.

The following example illustrates the invention without restricting it in any way:

EXAMPLE 1

A tube reactor which could be heated by means of a salt melt was charged with 10.8 g of a catalyst consisting of 55% by weight of ZnO and 45% by weight of $CaCO_3$ in the calcite modification (in each case determined in the form of the oxides in the ignited catalyst composition). At a temperature of 400° C., a mixture of 46 standard l/h of nitrogen and 3.44 g/h of R-citronellol having an enantiomeric excess of 95% ee was passed over the bed. Citronellal having an enantiomeric excess of R-citronellal of 95% ee was obtained in a selectivity of 75.5% at a conversion of 50.2%.

The invention claimed is:

1. A process for preparing optically active aldehydes or ketones which have from 3 to 25 carbon atoms and at least one racemizable stereocenter by in the α and/or β position relative to the carbonyl group catalytic dehydrogenation of the corresponding optically active primary or secondary alcohols in the gas phase in the presence of a catalyst, comprising zinc and calcium in oxidic form and/or in form of their carbonates.

2. The process according to claim 1, wherein the catalyst comprising zinc oxide and calcium carbonate is used.

3. The process according to claim 1, wherein the catalyst whose active component comprises from 30 to 60% by weight of zinc oxide and from 40 to 70% by weight of calcium carbonates is used.

4. The process according to claim 2, wherein the calcium carbonate is present in the calcite modification.

5. The process according to claim 1 for preparing branched or unbranched open-chain or monocyclic aldehydes or ketones.

6. The process according to claim 1 for preparing optically active 2-methylbutan-1-al, 3,7-dimethyloct-6-en-1-al, 3,7-dimethyloctan-1-al, 8-p-menthen-3-one, p-menthan-3-one, 2-methylcyclohexanone, 3-methylcyclohexanone, 2-methylcyclopentanone, 3- methylcyclopentanone, 2,6-dimethylcyclohexanone or 2,3-dimethylcyclohexanone.

7. The process according to claim 1 for preparing optically active citronellal from optically active citronellol.

8. The process according to claim 1, wherein the enantiomeric excess (ee) of the aldehyde or ketone obtained corresponds to at least 90% of the enantiomeric excess of the alcohol used.

9. The process according to claim 1, wherein the dehydrogenation is carried out at a temperature in the range from 250 to 600° C.

10. A process for preparing optically active menthol which comprises the preparation of optically active citronellal according to claim 1, and followed by cyclization of said citronellal to form isopulegol and subsequent hydrogenation.

11. The process according to claim 1, wherein the catalyst comprising zinc oxide and calcium carbonate is used.

12. The process according to claim 11, wherein the catalyst-whose active component comprises from 30 to 60% by weight of zinc oxide and from 40 to 70% by weight of calcium carbonates is used.

13. The process according to claim 12, wherein the calcium carbonate is present in the calcite modification.

14. The process according to claim 13 for preparing branched or unbranched open-chain or monocyclic aldehydes or ketones.

15. The process according to claim 14 for preparing aldehydes or ketones which have a stereocenter in the α and/or β position relative to the carbonyl group.

16. The process according to claim 15 for preparing optically active 2-methylbutan-1-al, 3,7-dimethyloct-6-en-1-al, 3,7-dimethyloctan-1-al, 8-p-menthen-3-one, p- menthan-3-one, 2-methylcyclohexanone, 3- methylcyclohexanone, 2-methylcyclopentanone, 3- methylcyclopentanone, 2,6-dimethylcyclohexanone or 2,3-dimethylcyclohexanone.

* * * * *